United States Patent [19]

Kamp

[11] Patent Number: 4,748,978
[45] Date of Patent: Jun. 7, 1988

[54] THERAPEUTIC DRESSING HAVING MINERAL COMPONENTS

[76] Inventor: Herman F. Kamp, 7th Floor, Arcadia Centre, Arcadia, Transvaal Province, South Africa

[21] Appl. No.: 781,098

[22] Filed: Sep. 27, 1985

[30] Foreign Application Priority Data

Sep. 27, 1984 [ZA] South Africa ............... 84/7613

[51] Int. Cl.[4] ........................................ A61L 15/00
[52] U.S. Cl. ............................ 128/156; 604/359; 604/368; 604/378; 428/241; 428/454; 502/80; 501/1
[58] Field of Search ............... 128/155, 156; 604/359, 604/360, 368, 378; 428/241, 247, 454; 502/80

[56] References Cited

U.S. PATENT DOCUMENTS

| | | | |
|---|---|---|---|
| 2,750,944 | 6/1956 | Tollstrup | 128/290 |
| 3,340,875 | 9/1967 | Dudley et al. | 128/290 |
| 3,935,363 | 1/1976 | Burkholder et al. | 604/368 |
| 3,966,641 | 6/1976 | Csater et al. | 502/80 |
| 4,460,642 | 7/1984 | Errede et al. | 428/283 |

FOREIGN PATENT DOCUMENTS

| | | | |
|---|---|---|---|
| 8101643 | 6/1981 | World Int. Prop. O. | 604/360 |
| 1155440 | 6/1969 | United Kingdom | 128/156 |

OTHER PUBLICATIONS

Browne, J. E. et al., "Characterization and Adsorptive Properties of Pharmaceutical Grade Clays", J. of Pharm. Sci., vol. 69, 7, (1980) pp. 816-823.

*Primary Examiner*—Richard J. Apley
*Assistant Examiner*—Paul Prebilic
*Attorney, Agent, or Firm*—Dressler, Goldsmith, Shore, Sutker & Milnamow, Ltd.

[57] ABSTRACT

The invention concerns a therapeutic dressing comprising an elongated flexible permeable support and a mixture of mineral components comprising 16 to 24% by mass of South African bentonite, 16 to 29% by mass of Kaolinite and 47 to 68% total by mass of South African illite and/or attapulgite, which mixture has been rendered into paste-form by the addition of at least an equal part by weight of a liquid mixture comprising 6 to 10 parts by mass of water and 6 to 2 parts by mass of glycerine.

4 Claims, 1 Drawing Sheet

THERAPEUTIC DRESSING HAVING MINERAL COMPONENTS

This invention relates to therapeutic dressings, in particular dressings for treating burns.

Skin injuries involving inflammation, particularly burn wounds, have been treated in a number of ways.

In the so-called exposure method, the burn wound is left open without any covering, dressing or bandage. Disadvantages of this method include a delay in epithelication due to drying occurring. Also a delay before removal of the eschar may allow secondary infection to occur. The inability to remove devitalised burn tissue safely and early can lead to increasing gram negative bacterial infection. Extensive fluid loss can occur from an apparently dry eschar. Also the heat taken up by evaporation accounts particularly for an excessive calorific expenditure in seriously burned patients.

With the alternative of using absorbent dressings, infection and an increase in wound depth tend to arise. Also extensive fluid loss takes place from a dressed burn wound with attendant heat loss. For example, when using dressings consisting of plain or medicated gauze covered by a plurality of layers of cotton wool, fluid from the wound soon premeates to the surface from where it is evaporated at a rapid rate. Also heat of inflammation arises and, with the moisture, creates a very favourable medium for bacterial proliferation.

Recently, there have been difficulties found with the use of antibiotic creams in the treatment of burn patients.

Because of these problems, I previously invented a composition for treating skin injuries. The composition causes cooling of the injured area to a temperature below the normal skin temperature and progressively premits the temperature to increase to a value in the vicinity of 37° C., which is higher than normal skin temperature but favourable to the proliferation of normal skin bacteria.

The composition is a mixture of mineral components comprising South African bentonite, kaolinite and South African illite, which mixture was rendered into paste form by the addition of a liquid mixture comprising of water and glycerine. The composition may be provided with a backing layer, eg gauze. Reference may be had to British Pat. No. 1,155,440, for details of this earlier invention, and the method by which the application of a clay to a burn works. That specification also discloses that the composition conveniently comprises 25 to 38% of South African bentonite, 30 to 50% by weight of kaolinite and 18 to 30% by weight of South African illite.

This prior composition is applied to the exterior of the skin of a patient who has suffered from burns. It has been found that this composition is very suitable for treating burn injuries. However, the composition has always been supplied in standard sizes, such as 200 mm by 130 mm. Where the burn area to be treated exceeded this size, two or more dressing were applied.

The application of more than one standard size dressing to wounds, as well as difficulties which arise where two dressings are applied to a wound and joined together, is not convenient for the patient or for the medical person applying the dressings. Furthermore, such dressings were thick and extremely heavy, this being partially determined by the necessity to avoid the dressing breaking during application.

The present invention is concerned with a dressing which is less heavy than that used before and which can avoid problems previously associated with the overlap of two separate dressings.

The present invention provides a therapeutic dressing said dressing comprising an elongated flexible permeable support, and a mixture of mineral components comprising 16 to 24% by mass of South Africa bentonite, 16 to 29% by mass of kaolinite and 47 to 64% total by mass of South African illite and/or attapulgite, which mixture has been rendered into paste-form by the addition of at least an equal part by weight of a liquid mixture comprising 6 to 10 parts by mass of water and 6 to 2 parts by mass of glycerine. The international committee for nomenclature has named "attapulgite" as "palygorskite".

The dressing can be used for any suitable therapeutic treatment, particularly the treatment of burn wounds, other wounds such as varicose ulcers, decubitus ulcers (bedsores) and lesions.

The present invention enables the breakdown or autolysis of damaged tissues to be controlled and limits damage to small blood vessels and soft tissue while ensuring conservation of superficial subcutaneous blood vessels and areolar fatty tissue. Sufficient oxygen can reach the injured area from small arteries and capillaries thereby promoting the healing of the wound. The dressing produces a marked decrease in the transpiration rate compared with non-dressed skin. The decrease can be to as low as 3 to 5% of the defatted skin value.

Readings can be taken on an evaporimeter of fluid loss from a burn wound with the eschar uncovered and fluid loss with the wound covered by a composition in accordance with the invention. Reductions of about 80% of the insensible fluid loss are possible.

Kaolinite is a crystalline mineral of the two layer type (sheet structures composed of units of one layer of silica tetrahedrons and one layer of alumina octahedrons) which is equidimensional. Generally it consists of about 80 to 85% kaolinite, about 10% of quartz as well as feldspar. South African bentonite is a crystalline smectitic clay mineral of the three layer type (sheet structures composed of two layers of silica tetrahedra and one central dioctahedral or trioctahedral alumina layer) having an expanding lattice. South African illite is a crystalline hydrous mica clay mineral of the three layer type (sheet structures are composed of two layers of silica tetrahedra and one central dioctahedral or trioctahedral layer) with a non-expanding lattice. Attapulgite (Palygorskite) is an active layered silicate clay mineral. It is very absorbent and thixotropic it comprises minute rectangular hollow needles. It is a fibrous clay mineral typically of formula: $(OH_2)_4.Mg_5Si_8O_{20}.(OH)_2.4H_2O$.

The particle size distributions, of a typical sample of kaolinite, illite and bentonite are as follows:

TABLE I

| Particle Size in Microns | Percentage Material Finer than Particle Size Shown | | |
|---|---|---|---|
| | Kaolinite | Illite | Bentonite |
| 1,200 | 100 | — | — |
| 600 | 99.9 | — | — |
| 200 | 99.8 | — | — |
| 100 | 99.6 | — | — |
| 60 | 99.5 | — | — |
| 37 | 99.3 | — | — |
| 20 | 89.9 | 97.6 | 99.4 |
| 10 | 66.8 | 95.9 | 93.9 |

TABLE I-continued

| Particle Size in Microns | Percentage Material Finer than Particle Size Shown | | |
|---|---|---|---|
| | Kaolinite | Illite | Bentonite |
| 6.3 | 50.7 | 87.6 | 93.1 |
| 2 | 29.1 | 84.0 | 77.0 |
| 0.63 | 20.8 | 77.0 | 61.6 |

A dry sieve analysis, determined after drying the clays at 110° C., gave the following results:

TABLE II

| Tyler Sieve (Mesh) | Particle Size in Microns | Percentage Material Finer Than Particle Size Shown | | |
|---|---|---|---|---|
| | | Kaolinite | Illite | Bentonite |
| 35 | 420 | 99.8 | 99.7 | 99.7 |
| 48 | 297 | 99.6 | 99.4 | 99.6 |
| 60 | 250 | 99.4 | 99.0 | 99.6 |
| 100 | 149 | 99.2 | 96.0 | 99.5 |
| 150 | 105 | 98.6 | 87.4 | 99.2 |
| 200 | 74 | 98.0 | 73.1 | 98.2 |

Typical properties are as follows:

TABLE III

| Component | pH | water binding capacity (Enslin value), cc/100 g clay. |
|---|---|---|
| Kaolinite | 8.4 | 112 |
| SA. Bentonite | 8.6 | 197 |
| Attapulgite | 8.2 | 228 |
| Illite | 7.7 | 250 |
| Mixture of Example 1, below | 8.7 | 160 |

From the water binding capacity values (i.e. the Enslin values) given above in Table III, it will be noted that the Enslin value for a mixture (160) as indicated in that Table, is different from the value (i.e. 195,3) which would be expected on an average of the parts combined. This indicates that the composition in accordance with the invention displays a synergistic effect, and has properties which are different from the aggregate of the properties of the various components. Likewise the pH of the mixture (8,7) as indicated in Table III is different from the expected average value (8,4). The various ingredients of the composition of this invention cannot individually or in aggregate achieve the properties of the composition of this invention unless combined with each other in the manner indicated above.

The water binding capacities (the Enslin values) of the samples were determined by means of an Enslin apparatus. Determinations were made with 0.3 g clay previously dried at 110° C. and the measurements were made in a constant temperature room (20° C.). In all cases, constant readings were obtained after 30 minutes. The Enslin values (in cc/100 g clay) give a measure of the total amount of water absorbed and adsorbed.

It will be apparent to persons skilled in the art that mineral components having substantially the same characteristics as those set out above, may be used in accordance with this invention, regardless of where such components are found. In other words, the terms "Kaolinite", "South African Bentonite", "Attapulgite" and "South African Illite" should be understood to include mineral components having substantially the same characteristics as set out above, where ever they may be found.

The ratio of mineral components to the liquid mixture can be varied, depending on the absorptive/adsorptive power needed for the dressing, which in turn may vary for different types of wounds. The relative ratios of the water to glycerine conveniently may vary from 6 to 10:6 to 2, more usually from 8 to 10:4 to 2 parts of water to parts of glycerine.

The invention also provides a therapeutic composition, said composition being a mixture of mineral components comprising 16 to 24% by mass of South African bentonite, 16 to 29% be mass of kaolinite and 47 to 68% by mass of South African illite and/or attapulgite, which mixture has been rendered into paste-form by the addition of a substantially equal part by weight of a liquid mixture comprising 6 to 10 parts by mass of water and 4 to 2 parts by mass of glycerine.

A preferred mixture of mineral components for treating burn wounds comprises 18 to 23% by mass of South African bentonite, 18 to 23% by mass of kaolinite and 54 to 64% by mass of illite and/or attapulgite.

A particularly prefered mixture comprises about 22 to 23% by mass of kaolinite, about 22 to 23% by mass of South African bentonite and about 55 to 56% by mass of either South African illite or attapulgite. The mixture may contain about 15 parts by mass of liquid mixture to 13 parts by mass of mineral components.

Preferably an anti-fungal agent is present. Methyl parahydroxybenzoate, eg as sold by the trade name Nipogen M may be used. The anti-fungal agent may be present in an amount of 0.04 to 0.06% by weight of the total composition.

In order to prepare the dressing in accordance with the invention, the minerals may be mixed together and formed into a paste by adding the water and glycerine. Thereafter, the flexible, permeable support, such as a backing layer (eg gauze) may be coated with the so-formed mineral mixture. Once the mixture has been applied to the carrier, the dressing so formed may be wound into a roll and/or folded back on itself several times so that the finished dressing, which will cover a substantial area, occupies a compact space. The dressing so formed may be packed in sealed containers which can be sterilized. For example, packages of plastics or metal foil or the like can be provided around the dressings and sealed until required.

The invention further provides a method of preparing a therapeutic dressing, which comprises preparing a mixture of mineral components comprising 16 to 24% by mass of South African bentonite, 16 to 29% by mass of Kaolinite and 47 to 68 total by mass of South African illite and/or attapulgite, admixing this mixture with a liquid mixture comprising 6 to 10 parts by weight of water and 6 to 2 parts by weight of glycerine to form a paste, applying the paste to an elongated flexible permeable support and packaging the dressing thereby obtained.

Thus, the mineral components may be prepared commercially by the grinding of their larger rock formations. Thereafter they may be mixed with each other in the stated proportions so as to form the mineral mixture. The mineral components can be mixed thoroughly in any suitable mixing apparatus, until a smooth consistancy is attained. The liquid mixture is then prepared separately, by mixing the water and glycerine in the stated proportions. Thereafter the mineral and liquid mixtures are worked in together in known manner, to form a soft, smooth paste.

The liquid mixture may be prepared in the following manner: First an anti-fungal agent is dissolved in a small quantity of the total amount of water, if necessary by boiling. The glycerine is added to the remaining volume of cold water and stirred well. The solution of the dissolved anti-fungal agent is added to the water glycerine mixture and stirred well. Thereafter the liquid mixture and mixture of mineral components are admixed together to provide a smooth paste.

The composition may be moulded into dressings of about 0,25 to 0,8 cm, preferably 0,28 to 0,32 cm thick, and in different sizes. The dressing may be provided with one or more backing layers, such as of gauze. If the backing layers are highly liquid absorbent, the amount of liquid mixture provided in the composition according to the invention, should be correspondingly increased, so that the amount of liquid in the mineral composition of the final dressing, would be not less than the amount indicated above, notwithstanding the fact that the backing layer or layers have absorbed a certain amount of liquid.

The dressing may be covered by a sheet of liquid impervious material, such as a cellulosic sheet material, and formed into a closed package. The finished dressing may then be inserted into a polyethylene and/or aluminium foil packaging, sealed and sterilized. Preferably a high density polyethylene bag is used, which is heat sealed with removal of air during sealing.

A plurality of dressings or poultices, sealed within polyethylene bags, may be packed into a suitable container, the container sealed with autoclaving tape, may then be sterilised with gamma radiation. Thereupon the dressings may be removed, cooled and suitably packed and the package sealed for marketing and use.

With the present invention, the sealed package can be opened and the dressing applied to the patient with the mineral components in contact with the patients skin. By having an elongated broad dressing, the dressing can cover the entire part of the patient to be treated and can be cut to size as necessary. The dressing is of lighter weight than the prior dressings known to the applicant and is very convenient to apply to the limbs of a patient, and especially to burnt parts of a childs skin. Evaporation of fluid from the injured area and regulation of the temperature to the injured area is controlled with the dressing, with the result that micro-circulation is maintained and healing expedited.

Instead of having a single layer of permeable flexible material as the support, the support may be folded over both sides of the dressing. The dressing may be made in standard lengths and widths, and cut as desired. The edges where the dressing has been cut may be covered with strips of flexible permeable material.

The elongated flexible support for the dressing of the invention can be surgical gauze or other suitable material, which can be provided in one or both sides of the mixture of mineral and liquid components. A flexible non-stick impermeable material, eg a plastics sheet may cover the entire area of each side of the dressing. This makes the handling of the dressing, and its removal from the outer container package much easier and not messy when fitting and cutting to size. The non-stick impermeable material also helps handling when covering the cut edges of the dressing with gauze strips after cutting to size.

The flexible non-stick impermeable material, eg plastic sheet material, should be removed before use. For example the sheet on one side can be removed, with that side being applied to the wound. Thereafter the other side can be removed.

Generally speaking the mode of use of the dressings, the working thereof and the advantages given for the dressings of the UK Pat. No. 1,155,440 apply to the dressings of the present invention. Reference may be had thereto. Thus the dressing causes initial cooling, followed by allowing the temperature to rise to about 37° C.

After applying the dressing to a patient, the outside of the dressing may be wetted from time to time to cool the burn wound down. A control of the temperature of the skin of the patient, within reason, can thereby be obtained. This is important for burn treatment. The progressive increase in temperature may be effected during a period of between 1 and 4 hours. By a reapplication of a cold dressing, a complete cycle of cooling and gradual rise in temperature can be carried out every 24 hours. The coolest temperature conveniently may be 10° to 15° C., depending on the nature of the injury. The fluid is able to escape from the wound via heat damaged capillaries and vesicles. The dressing allows blood to flow through the more normal vessels and lesser veins while the lymphatics will experience a similar opening effect with clearing of oedema (for which the spelling "edema" is also used) fluid.

The following non-limiting Example illustrates the invention.

EXAMPLE

A mixture of mineral components was made by mixing together 2 parts by mass of South African Bentonite (22,22%) 2 parts by mass of Kaolinite (22,22%) and 5 parts by mass of Attapulgite (55,56%). This mixture was made into paste form by mixing with about 10 parts by mass of a liquid mixture consisting of 7 parts by mass of water and 3 parts by mass of glycerine.

The paste obtained was applied in a 3 mm thick layer to one half of the width of a length of surgical gauze. The other half of the width of gauze was then folded over on the first half to provide a dressing with the paste between two layers of gauze.

A separate sheet of therapeutically acceptable plastics film was applied on either side of the dressing and adhered to the pasty outer surface of the dressing protruding through the gauze.

The dressing was placed in a plastics package, sealed and sterilized. In use, the package is opened, one of the sheets of plastic film is removed and that side applied over the wound. Thereafter the plastic film on the other side is removed.

The dressing draws fluid out of the wound. Cooling of the wound takes place. Water can be applied to the outside of the dressing to obtain additional cooling.

The betonite had an oil value of 60, the kaolinite had an oil value of about 50 and the attapulgite had an oil value of over 60. All three materials were obtained from G & W. Base Minerals (Pty) Limited.

The Enslin values of the three clays used were determined on air dry samples. The values given represent the total water absorption of the clays at saturation point and are given in percentage of dry mass. The values were as follows:

| Bentonite | 197 |
| Attapulgite | 228 |
| Kaolinite | 110 |
| Mixture | 160 |

The Kaolinite used was mined in the Mossel Bay area of South Africa. It is a natural pure kaolin with a light cream colour and contains minor amounts of felspar and quartz. On analysis it contained 53% $SiO_2$; 31% $Al_2O_3$; 1,5% $Fe_2O_3$; 0,1% of each of CaO and MgO; 0,2% of each of $K_2O$ and $Na_22$; 0.9% of $TiO_2$; 1,0% of water and had an ignition loss of 11.7%.

DESCRIPTION OF THE DRAWINGS

An embodiment of the invention is illustrated in the accompanying drawings in which.

In these figures a dressing shown generally at 10 comprises a layer of a paste 12 according to the invention supported between layers of gauze 14, 14.1 Protective layers of plastic film are shown at 16, 16.1.

Figure 1:
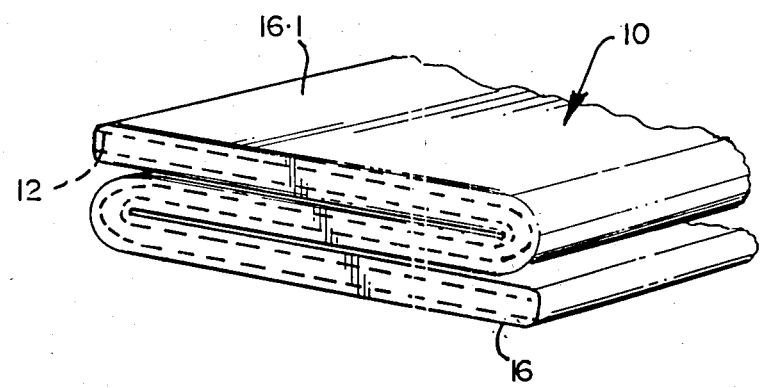
FIG. 1 is a three dimensional view of a folded dressing according to the invention.
Figure 2:
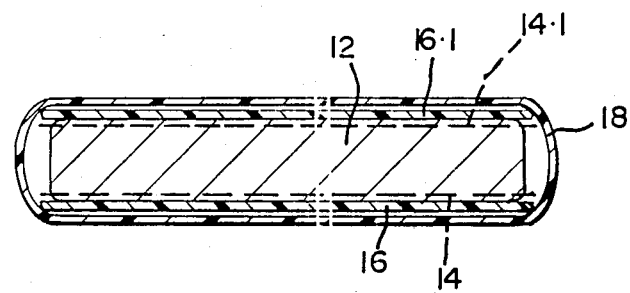
FIG. 2 is a section across another embodiment of a dressing according to the invention in a sterilised package.

In FIG. 2, the dressing is as described in FIG. 1 outer package is shown at 18.

The mass of a dressing in accordance with the above Example, and as illustrated in the drawing was only 0,5 g/"$cm^2$". The mass of a commercial dressing in accordance with my earlier invention of British Pat. No. 1,155,440 was 2,1 "$g/cm^2$". The dressing of the present invention therefore has the substantial advantage of being of much lighter mass.

The following is the result of an actual treatment for burns:

A woman aged 35 years burned both feet and lower legs in very hot water. When first seen 5 days later the right leg appeared more seriously injured and was therefore selected for treatment with the dressing of Example 1 above, secured with only two windings of gauze bandage to allow for periodical cooling and normal heat loss from the wound. This was changed daily but, in addition, the dressing (in position) was cooled down every eight hours with a spray gun.

The left leg was treated with a topical antibacterial cream changed daily. Ten days later this leg showed areas of full thickness depth of injury and had to be dissected and grafted. Healing was complete 23 days after injury.

The right leg progressed with no pain and no extension in depth and was healed in 18 days. A clear advantage was therefore obtained using the product of the invention compared with a commercially available antibacterial cream. Had the treatment with the product of the invention been applied sooner after the burn injury took place, the healing time would have been reduced still further, probably by about four days or even more.

I claim:

1. A therapeutic dressing comprising an elongated flexible permeable support and a mixture of mineral components comprising 16 to 24% by mass of South African bentonite, 16 to 29% by mass of kaolinite and 47 to 64% total by mass of at least one material selected from the group consisting of South African illite and attapulgite (palygorskite based on the total mass of the mineral components, which mixture has been rendered into a paste-form by the addition of at least an equal part by weight of a liquid mixture comprising 6 to 10 parts by mass of water and 6 to 2 parts by mass glycerine, said dressing having a mass of less than 2.1 $g/cm^2$.

2. A therapeutic dressing as claimed in claim 1, wherein there are 8 to 10 parts by mass of water and 4 to 2 parts by mass of glycerine.

3. A therapeutic dressing as claimed in claim 1, wherein the mixture of mineral components comprises 18 to 23% by mass of South African bentonite, 18 to 23% by mass of kaolinite and 54 to 64 total by mass of South African illite and/or attapulgite (palygorskite).

4. A therapeutic composition comprising 16 to 24% by mass of South African bentonite, 16 to 29% by mass of kaolinite and 47 to 68% total by mass of at least one material selected from the group consisting of South African illite and attapulgite (palygorskite) based on the total mass of the mineral components, which mixture has been rendered into paste-form by the addition of at least an equal part by weight of a liquid mixture comprising 6 to 10 parts by mass of water and 6 to 2 parts by mass of glycerine, said composition, when applied to a flexible permeable support, producing a dressing having a mass of less than 2.1 $g/cm^2$.

* * * * *